United States Patent [19]
Murphy, Jr.

[11] Patent Number: 5,165,417
[45] Date of Patent: Nov. 24, 1992

[54] LUNG SOUND DETECTION SYSTEM AND METHOD

[76] Inventor: Raymond L. H. Murphy, Jr., 38 Cypress Rd., Wellesley, Mass. 02181

[21] Appl. No.: 406,152

[22] Filed: Sep. 12, 1989

[51] Int. Cl.[5] .............................. A61B 7/00
[52] U.S. Cl. ................... 128/716; 128/710; 128/773; 181/126; 181/131; 381/67
[58] Field of Search ............. 128/773, 774, 780, 782, 128/700, 710, 716; 181/126, 131; 381/67

[56] References Cited

U.S. PATENT DOCUMENTS

| | | | |
|---|---|---|---|
| 4,193,393 | 3/1980 | Schlager | 128/710 |
| 4,878,360 | 7/1989 | Palsgard et al. | 128/773 |
| 4,974,601 | 12/1990 | Tranjan et al. | 128/700 |

FOREIGN PATENT DOCUMENTS

| | | | |
|---|---|---|---|
| 8906932 | 8/1989 | PCT Int'l Appl. | 128/773 |

*Primary Examiner*—David M. Shay
*Attorney, Agent, or Firm*—Iandiorio & Dingman

[57] ABSTRACT

A system and method for automatically detecting an adventitious sound from a sound signal formed of a plurality of successive sound waves received from a patient including establishing at least one of a predetermined time interval and a threshold signal value based on an average signal value of at least a portion of a sound signal, sequentially comparing the sound waves to at least one of the threshold signal value and the predetermined time interval to identify a first wave having at least one of an amplitude at least as large as the threshold signal value and a duration falling within the predetermined time interval, and identifying an adventitious sound when at least one consecutive wave following the first wave has at least one of an amplitude at least as large as the threshold signal value and a duration falling within the predetermined time interval.

19 Claims, 12 Drawing Sheets

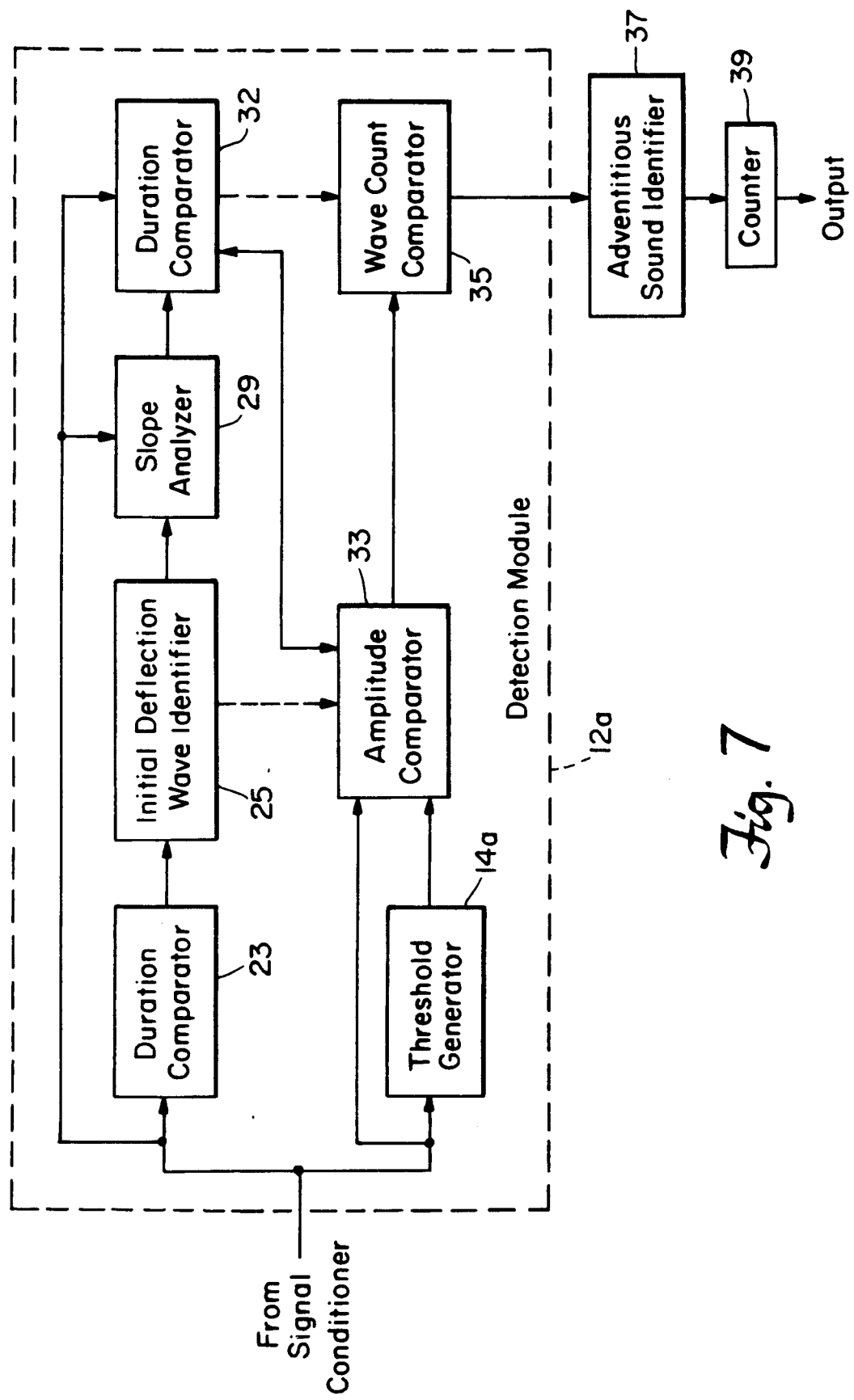

LUNG SOUND DETECTION SYSTEM AND METHOD

FIELD OF INVENTION

This invention relates to a diagnostic method and apparatus for detecting breathing abnormalities in humans to diagnose lung disorders and more particularly to such an apparatus and method which automatically detects adventitious lung sounds.

BACKGROUND OF INVENTION

Listening to various adventitious or abnormal breathing sounds has proven to be an important diagnostic tool for detecting and monitoring certain types of lung diseases. Abnormal pulmonary sounds are generally detected by placing a stethoscope over selective areas of a patient's chest and listening for the sounds directly. The type of abnormal sound, its location, and its frequency of occurrence are used to make determinations of the type of disease and its severity.

The detected sounds are typically classified into normal lung sounds or adventitious (abnormal) sounds, usually divided into continuous or discontinuous sounds depending on their duration. Continuous sounds are further divided into wheezes, which are high-pitched, hissing sounds and rhonchi, which are low-pitched, snoring sounds. Discontinuous sounds are similarly divided into coarse crackles, which are short intermittent explosive sounds having a low pitch, or fine crackles, which are distinguished from coarse crackles in that they are less loud, shorter in duration, and higher in pitch. Other adventitious sounds include pleural friction rub and bronchial breathing.

Generally, it is a difficult task for an observer to detect accurately various lung sound abnormalities, since they are frequently of short duration, sometimes of relatively low amplitude, and generally mixed in with normal breathing sounds, which sometimes obscure the abnormal sounds. Furthermore, the task of classifying, quantifying and documenting lung sounds is difficult to accomplish with a stethoscope. Observers vary greatly in their abilities in this regard, making diagnosis less reliable.

An apparatus which forms visual waveforms representing the breathing sounds of a patient using a time-expanded scale has been disclosed by the present inventor in U.S. Pat. No. 3,990,435. This apparatus permits a trained observer to visually delineate the abnormal sounds from normal sounds. This has greatly improved diagnostic accuracy and helped clarify the previously confused lung sound nomenclature. Diagnosis, however, depends on the observer to properly sort and distinguish the different abnormal lung sounds from the normal lung sounds detected at various locations. The manual sorting of lung sounds visually or acoustically is a tedious task whose accuracy depends on the experience and alertness of the observer.

Another method of adventitious sound detection employs one or more bandpass filters to selectively detect sounds in preselected frequency ranges. Abnormal sound identification is based on the percentage of the total sample made up of sounds in the selected ranges. This technique is very unreliable; many of the adventitious sounds have components in the same or overlapping frequency ranges. As a result, the technique often cannot distinguish the different types of sounds, especially when more than one type is present.

SUMMARY OF INVENTION

It is therefore an object of this invention to provide a system for automatically identifying adventitious (abnormal) sounds from a patient.

It is a further object of this invention to provide a system for automatically identifying crackles, wheezes, rhonchi, squeaks and squawks.

It is a further object of this invention to provide a system for automatically counting such adventitious sounds.

This invention results from the realization that a simple, noninvasive and harmless way of analyzing illnesses associated with lung disease can be achieved by automatically identifying adventitious lung sounds in a patient by sequentially comparing each half cycle sound wave in a lung sound signal with predetermined wave duration and/or amplitude criteria to identify sounds based on a comparison of these results to expert analyses of typical sound signals of the different types of adventitious lung sounds.

This invention features a system and method for automatically detecting an adventitious sound from a sound signal formed of a plurality of successive sound waves received from a patient. The system features means for establishing at least one of a predetermined time interval and a threshold signal value based on an average signal value of at least a portion of the sound signal, and means, responsive to the means for establishing, for sequentially comparing the sound waves to at least one of the threshold signal value and the predetermined time interval to identify a first wave having at least one of an amplitude at least as large as the threshold value and a duration falling within the predetermined time interval. Further included are means, responsive to the means for sequentially comparing, for identifying an adventitious sound when at least one consecutive wave following the first wave has at least one of an amplitude at least as large as the threshold signal value and a duration falling within the predetermined time interval.

Preferably, the system includes means for receiving the sound signal from a patient, which may be accomplished with an electronic stethoscope. Also included may be means for conditioning the sound signal to attenuate normal sounds. That may be accomplished with a filter for attenuating sound signals having frequencies lower than approximately 80 hertz and greater than approximately 2000 hertz. The system may further include means for storing a sample sound signal, which may include an analog sound signal sample. The means for conditioning the sound signal may also include means for digitizing that signal. Also included may be means for amplifying the sound signal.

Preferably, the system includes means for determining an average signal value of at least a portion of the sound signal, and means for generating a threshold value based on that average value. In that embodiment, there may further be included means for sequentially comparing the sound waves with the predetermined time interval to identify an initial deflection wave having a duration falling within the time interval. Further included may be means, responsive to the means for sequentially comparing the sound waves, for sequentially comparing the sound waves following the initial deflection wave to the threshold value, and means for identifying an adventitious sound occurring within the sound signal only when a plurality of consecutive sound waves including the initial deflection wave have an amplitude at least as large as the threshold value.

The system preferably also includes means for comparing the total sum of waves including the initial deflection wave and the number of consecutive sound waves thereafter having an amplitude at least as large as the threshold value to a predetermined wave count range. In that case, the means for identifying is preferably responsive to the means for comparing the total sum of waves for identifying an adventitious sound only when the total sum of waves is within the predetermined wave count range. That wave count range is preferably from two to sixteen waves.

The system may further include means for determining the initial slope of the wave following the initial deflection wave, and means, responsive to the means for determining the initial slope, for comparing the initial slope with the predetermined slope range to identify a wave following the initial deflection wave having an initial slope falling within that slope range. In that case, the means for identifying is preferably further responsive to the means for comparing the initial slope for identifying an adventitious sound only when the initial slope of the wave following the initial deflection wave is within the slope range.

The system may also include comparator means for comparing the individual durations of at least a portion of the sound waves following the initial deflection wave with the predetermined time interval. In that case, a counter is preferably included, responsive to the comparator, for resolving the number of consecutive sound waves including the initial wave having a duration falling within the predetermined time interval. The means for identifying may then be responsive to the counter means for identifying an adventitious sound only when a plurality of consecutive sound waves have a duration falling within the predetermined time interval.

In an alternative embodiment, the system may further include means for comparing the individual durations of the consecutive sound waves having a duration falling within the predetermined time interval to the duration of the previously occurring sound wave. In that case, the means for identifying may be further responsive to the means for comparing the duration of the consecutive sound waves for identifying an adventitious sound only when a plurality of successive sound waves following the initial deflection wave have progressively increasing durations. The predetermined time interval may be from approximately 0.125 to approximately 3.0 milliseconds. The system may identify the sound based on overall duration; a crackle lasting less than 25 milliseconds; a squeak or squawk lasting from 25 to 250 milliseconds; and a wheeze or rhonchus lasting more than 250 milliseconds. The other identification criteria may also be employed to further differentiate the type of adventitious sound.

DISCLOSURE OF PREFERRED EMBODIMENT

Other objects, features and advantages will occur to one skilled in the art from the following description of a preferred embodiment and the accompanying drawings, in which:

FIG. 7 is a more detailed schematic diagram of the system of FIG. 5 detailing the detection module.

Figure 1:
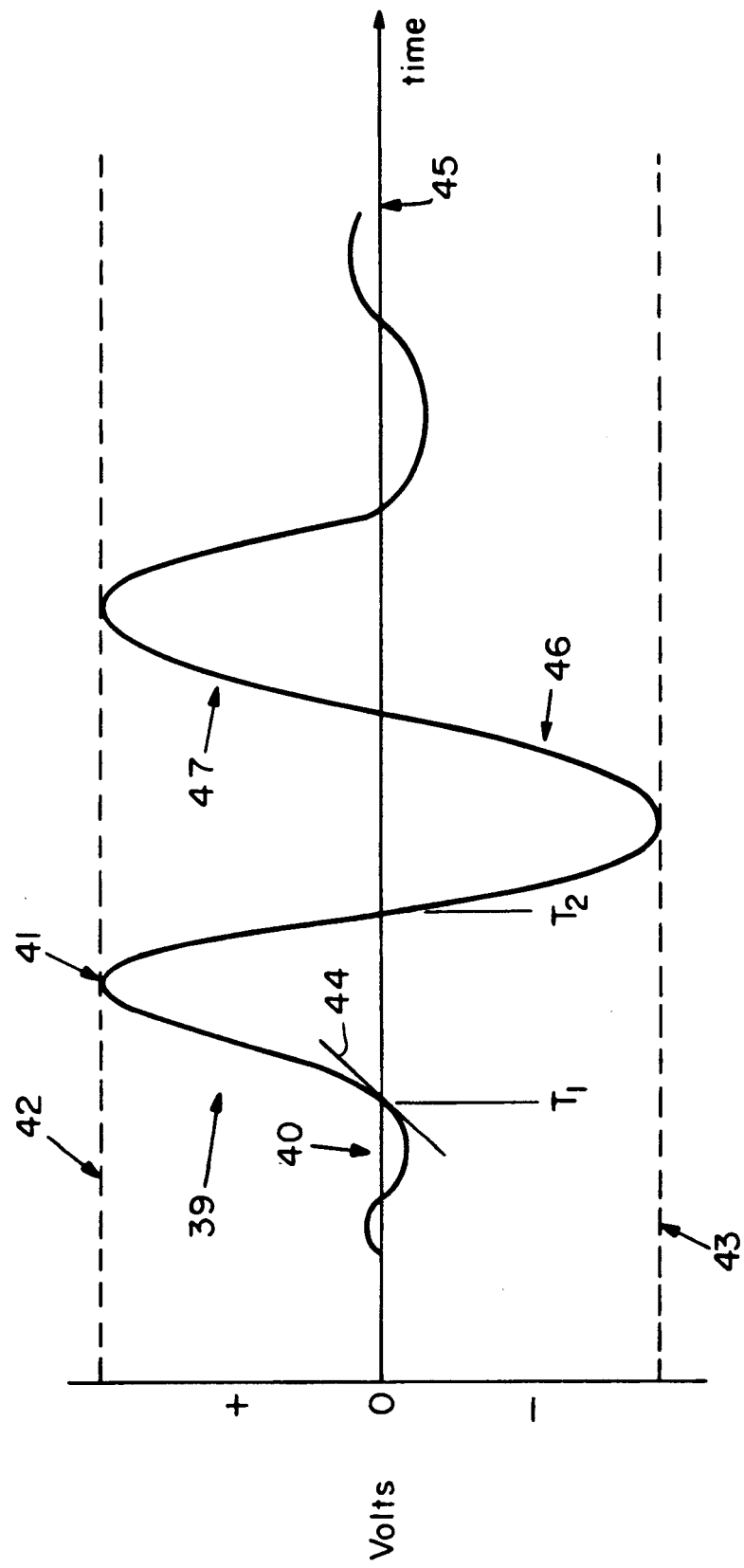
FIG. 1 is a waveform illustrating an abnormal lung sound illustrative of an adventitious sound detected by the system of this invention.

A lung sound detection system according to this invention automatically detects an adventitious sound from a sound signal received from a patient consisting of a number of sequential sound waves. An adventitious sound is identified from information derived from the durations of the individual sound waves or their amplitudes, or both. In one embodiment, when a preselected number of consecutive waves in the sound signal meet the established duration and/or amplitude parameters, the group of waves is identified as an adventitious sound. Preferably, an entire sound signal consisting of at least one inspiration and expiration cycle is checked in this manner, and the number and type of adventitious sounds occurring in the sound signal is determined.

There are many types of adventitious sounds which may be identified by the system and method according to this invention. Adventitious sound identification has always been an important diagnostic tool. However, until recently, uniform standards for identifying adventitious sounds did not exist. In U.S. Pat. No. 3,990,435, incorporated herein by reference, some of those different types of adventitious sounds were shown and described. The sounds called rales in that patent are now known as crackles. The different types of adventitious sounds have historically been identified by the physician using a stethoscope. In the referenced U.S. patent, a breath sound diagnostic apparatus was disclosed which visually displayed on a time-expanded scale a representation of lung sounds. That apparatus provided practitioners the ability to visually identify adventitious sounds.

The commonly occurring adventitious sounds may be briefly described as follows. Crackles are typically artifacts having a duration of less than twenty-five milliseconds. A crackle typically includes from two to sixteen consecutive half cycle sound waves each having a duration of from approximately 0.125 to approximately 3.0 milliseconds. Coarse crackles are relatively loud and low-pitched; fine crackles are softer, shorter, higher-pitched sounds. The durations of the half cycle waves in a crackle typically increase as the event progresses.

A wheeze is typically a continuous, high pitched polyphonic musical sound lasting at least 250 milliseconds. The sound may have two predominant frequencies, one centered between 350 and 500 Hz, and the other below that. The half cycle sound waves are typically relatively uniform throughout the artifact. A rhonchus is typically a continuous low pitched, snoring sound which is visually similar to a wheeze, with a duration of at least 250 milliseconds. The primary difference between the wheeze and rhonchus is the frequency; the rhonchus typically is monophonic, with a predominant frequency below 350 Hz. Squeaks and squawks are short high pitched chirping sounds with typical durations between twenty-five and 250 milliseconds. Visually, the wave form is relatively uniform. Thus, the system and method of this invention also contemplates identification based on sequential comparison of individual sound wave durations to establishd duration criteria based on the dominant frequencies or overall sound duration.

A further identification factor may be based on an analysis of the distribution of the half cycle sound wave amplitudes occurring in the sound signal. Normal lung sounds have a relatively random amplitude distribution. The wave amplitude distribution in a crackle has been found to be relatively narrow; the majority of the waves have similar amplitudes. On the other hand, the amplitude distribution in a typical rhonchus is wide; there are relatively even numbers of waves having several different amplitudes. Adventitious sound identification based on the amplitude distribution criteria may be used alone or in conjunction with one or more of the other criteria.

This invention thus provides for automatic identification of adventitious sounds based on the amplitude and/or duration of the half cycle sound waves forming the sound, as well as the overall duration of the artifact itself. The system and method of this invention provides the flexibility for identification based on these factors in accordance with established definitions of adventitious sounds.

In a preferred embodiment, a crackle is identified as follows: an average value of the sound signal is determined and a threshold value is generated from that average value. The individual sound waves of the sound signal are then compared to a predetermined time interval to detect an initial deflection wave having a duration falling within that interval. Once an initial deflection wave is identified, the lung sound detection system sequentially analyzes the sound waves immediately following the initial deflection wave to identify the adventitious sound.

In this preferred embodiment, the initial slope of the wave immediately following the initial deflection wave is preferably determined. The initial slope is defined as a slope of the wave immediately after the first zero crossing. If the slope is within a predetermined range of slopes, the system continues the analysis. If the slope does not fall within the selected range, the system returns to the duration analysis, looking for the next initial deflection wave.

When the slope is within the preselected range, the system determines the number of sequential waves following the initial deflection wave meeting established duration and amplitude criteria. A wave is identified as potentially part of an adventitious sound when it has an amplitude at least as large as the preestablished threshold value and a duration falling within the preselected range. The duration of each wave is also compared to the duration of the immediately preceding wave; a wave is identified as being potentially part of an adventitious sound only when its duration is greater than that of the preceding wave, as long as its duration stays within the preselected duration range.

The sound is then identified as a crackle by comparing the number of sequential waves having the established criteria to a preselected wave count. For example, the system may be enabled to identify a portion of the sound signal as a crackle when the number of consecutive waves including the initial deflection wave meeting the established criteria is between two and sixteen. If the number is less than two or greater than sixteen, the system does not identify the group of waves as a crackle and the operation returns to wave analysis for identification of the next initial deflection wave. Alternatively, the sequential wave count may continue for identification of continuous sounds. For example, the sound may be a wheeze or rhonchus if there are at least seventeen consecutive waves meeting the criteria. For continuous sounds, increasing duration is typically not used as a criterion. The system may then distinguish the specific type of continuous sound based on other criteria.

Adventitious sounds may be identified in other manners as is more fully described below. The above description of a preferred embodiment is simply one example of a rigorous sound signal analysis for adventitious sound identification.

There is shown in FIG. 1 an example of a portion 39 of a sound signal received from a patient. The portion includes successive half-cycle sound waves 40, 41, 46 and 47. Portion 39 illustrates a crackle; waves 40, 41, 46 and 47 are sequential waves which meet the criteria established for identification of such an adventitious sound. Wave 40 is an initial deflection wave, which is identified as a wave having a duration falling within a predetermined time interval. The duration of the wave is defined as the time between zero crossings, established by line 45.

After the identification of initial deflection wave 40, the system preferably determines initial slope 44 of next wave 41. The system identifies wave 41 as potentially belonging to an adventitious sound when its duration, or time between zero crossings, $T_2 - T_1$, falls within the predetermined range of durations. Alternatively, wave 41 may be identified when its amplitude is at least as large as previously established threshold value 42. For waves in the opposite direction, threshold value 43 having the same absolute value as threshold value 42 is established.

The duration and/or amplitude of successive waves is then compared to the preestablished criteria for determination of the number of consecutive waves having those criteria. Additionally, the system may compare the durations of the successive waves and identify a wave only when its duration is greater than the previous wave in the group identified as a potential adventitious sound. When the number of consecutive waves identified is at least two and no more than sixteen, the system identifies the wave group as a crackle. The analysis then continues with the next wave after the adventitious sound to look for the next initial deflection wave. Preferably, the system scans the entire sound signal in this manner and determines the number and type of adventitious sounds for use by the physician in diagnosis.

Figure 2A:
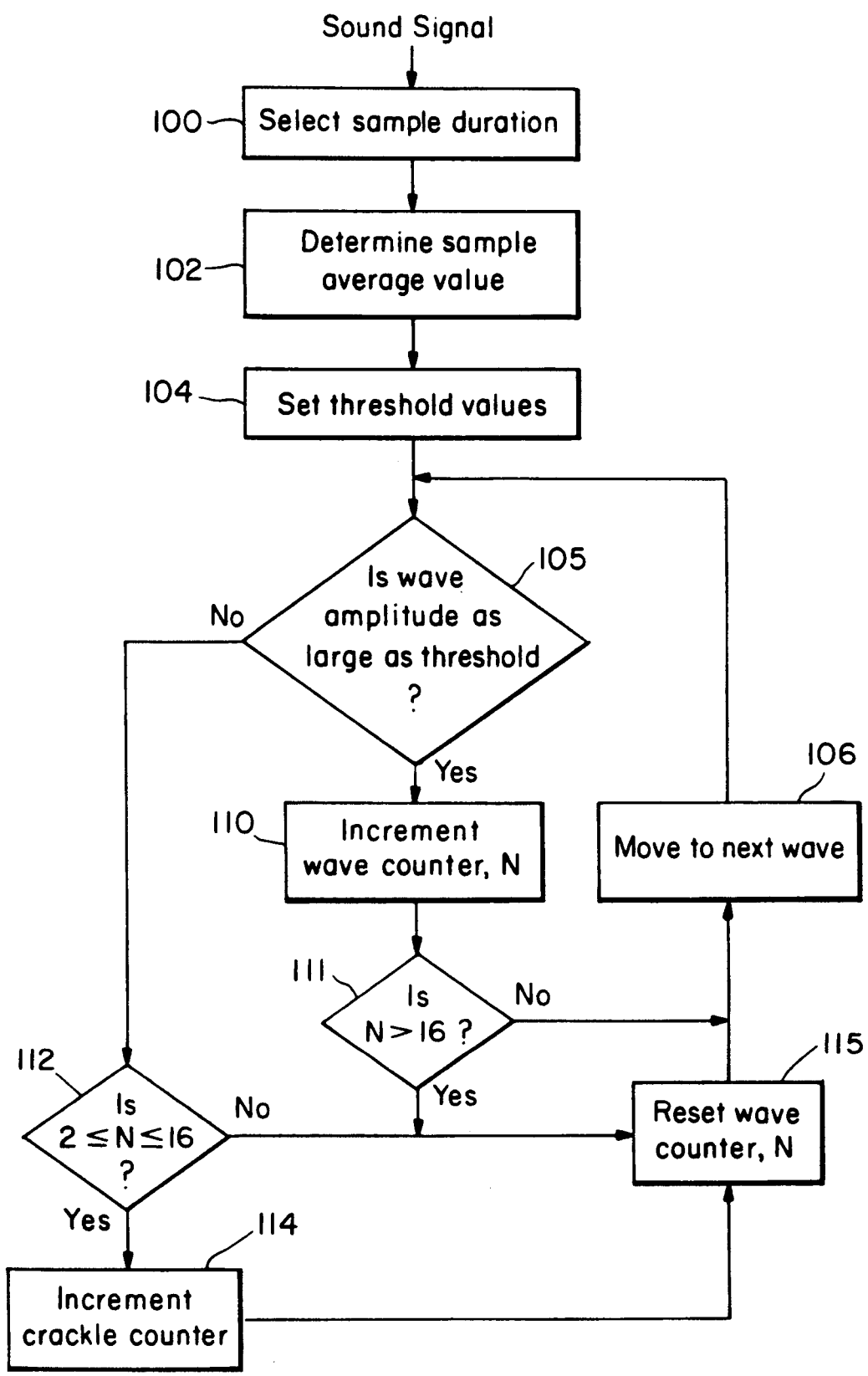
FIGS. 2A, 2B, 2C, 3A, 3B, 3C, 4A and 4B are flowcharts illustrating the operation of the system according to this invention.

Flow charts for embodiments of the system and method according to this invention are shown in FIGS. 2 through 4. In one embodiment, FIG. 2A, adventitious sounds such as crackles are identified by first selecting a sample of a predetermined duration from the sound signal, step 100. The sample duration may be a portion of or an entire inspiration and expiration cycle, or more than one such cycle. The sample average is determined, step 102, preferably as the root mean square of the signal value. The root means square is preferably the square root of the average square of the instantaneous magnitude of the voltages. This average value is then used to establish threshold values, step 104. As an example, threshold value that are plus and minus three times the average value have been found to be useful for identifying crackles. The threshold value may be established based on the operator experience, and previous patient history.

The system then compares sequentially the half cycle sound waves of the sample to the threshold values, step 105. If the wave amplitude is as large as a threshold, the system moves on to step 110, in which wave counter N is incremented. If N is greater than 16, N is reset, step 115. If N is not greater than 16, operation proceeds to an amplitude review of the next wave, steps 106 and 105. If the amplitude is not as large as the threshold, operation proceeds to step 112.

The total number N of consecutive waves including the first wave satisfying the identification criterion forms in this example the basis for identification. As a non-limiting example, to identify a crackle, N may be chosen as between 2 and 16. The number employed is based on expert evaluation of visual representations of an adventitious sound identified as a crackle. If N is greater than 16, the group of waves is not a crackle and operation returns to step 106 through step 115. If N is less than 16, and greater than 2, the crackle counter is incremented, step 114, the wave counter is reset, step 115, and operation returns to step 106 for analysis of the remainder of the sample.

Figure 2B:
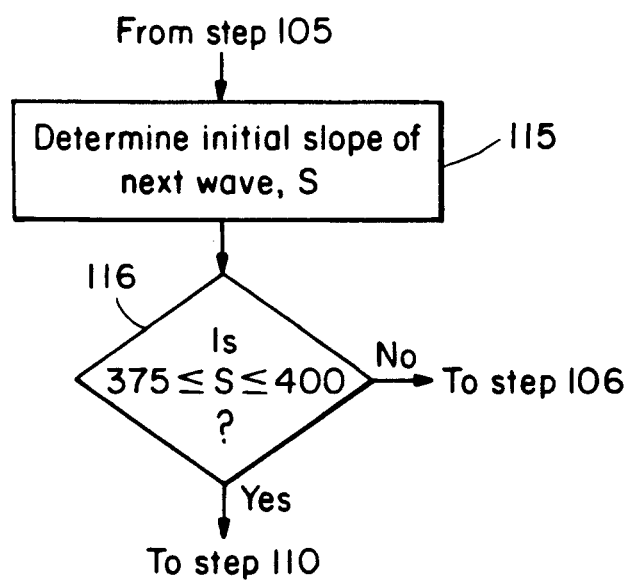

Two additional steps which may be added to the flow chart of FIG. 2A are shown in FIG. 2B. After a first wave having at least the threshold amplitude is identified, step 105, operation may continue to step 115 for a determination of the initial slope of the next wave. If slope S is between 375 and 400, as is more fully described below in conjunction with FIG. 7, the operation continues to step 110. Preferably, only the initial slope of the wave immediately following the first wave identified in step 105 is checked. Thus, steps 115 and 116 would be passed through only once—immediately after initial wave identification. After that, the system checks only the wave amplitude as described above in conjunction with FIG. 2A.

Figure 2C:
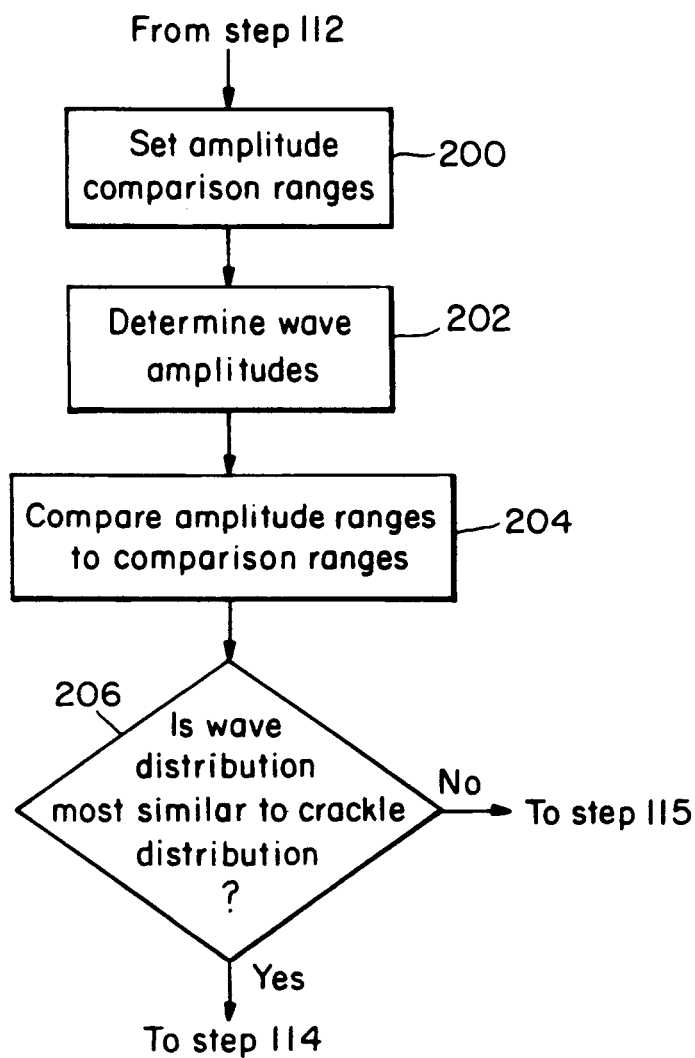

Another set of steps which may be added to the flow chart of FIG. 2A is shown in FIG. 2C. After the number N of waves satisfying the amplitude criterion are counted, step 112, operation may continue to step 200 for amplitude comparison range setting. Step 200 may comprise reading comparison ranges from a lookup table or allowing the operator to set the ranges as desired. The amplitude ranges may be established by plotting the number of waves having given amplitudes as is more fully described below in conjunction with FIGS. 8A through 8C. The result is similar to an expert system in that the system and method according to this invention may compare the wave amplitude distribution to that known to exist for the different types of adventitious sounds to identify the occurrence of that type of sound. Operation proceeds to step 202 in which the system determines the wave amplitudes and step 204 in which the determined amplitudes are compared to the established comparison ranges. The result is similar in effect to plotting the amplitude ranges as shown below.

In identification of crackles, step 206 is included for comparison of the wave distribution to that of a typical crackle. It should be understood that for identification of other types of adventitious sounds, the comparison may be made to known amplitude distributions for each of the types of adventitious sounds. The artifact may then be identified by comparison of the amplitude distributions to those established amplitude distributions. At step 206, if the distribution is more similar to crackle distribution, operation proceeds to step 114. If not, operation proceeds to step 115. For a system in which something other than a crackle, or more than just a crackle, is being monitored, rather than proceeding to step 115, the operation could proceed to additional steps similar to step 206 for a comparison of the wave distribution range to distributions for other types of adventitious sounds, for example, wheezes, rhonchi, squeaks and squawks.

Figure 3A:
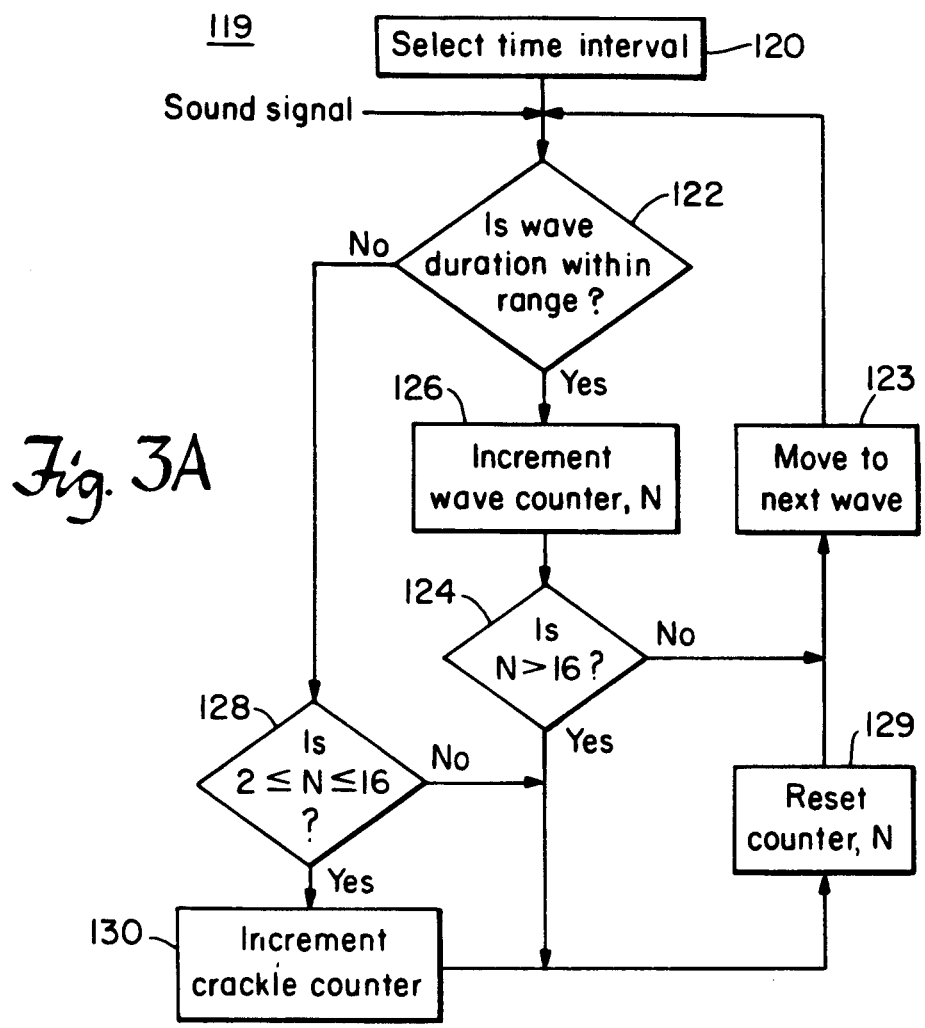
Figure 3B:
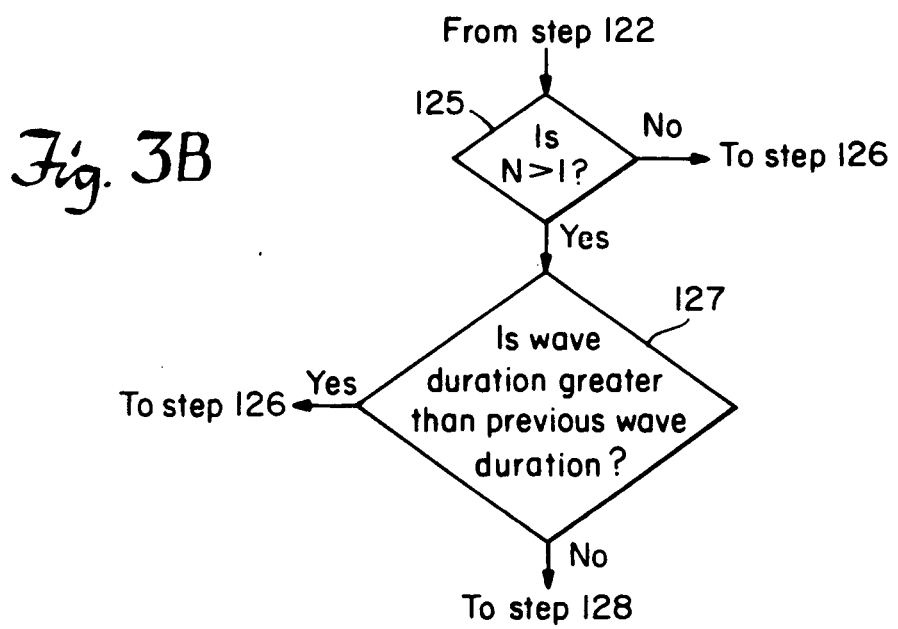
Figure 3C:
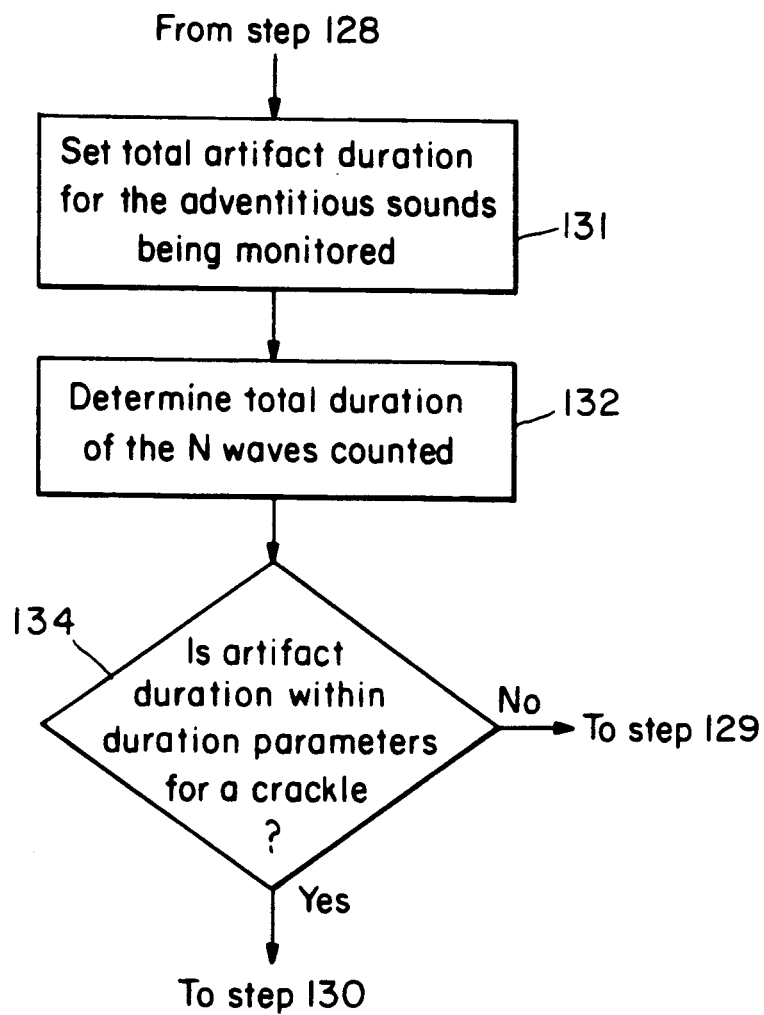

A flow chart for an alternative embodiment of the adventitious sound identification system is shown in FIGS. 3A, 3B and 3C. System 119 sequentially compares wave durations to a selected time interval and determines the number of sequential waves having a duration falling within that interval to identify an adventitious sound. After selection of a time interval for comparison to wave durations, step 120, operation proceeds to step 122, in which the wave durations are sequentially compared to the selected time interval. When a first wave having a duration within that range is found, operation continues to step 126, in which counter N is incremented. If N is not greater than 16, step 124, the monitoring loop continues through step 123. Steps 122, 126, 124 and 123 thus provide sequential wave duration monitoring. If the number of successive waves having a duration within the predetermined range of durations is greater than sixteen, step 124, the group is not a crackle and operation returns to step 123 through step 129 to begin looking for the next initial deflection wave.

After the sequential identification of a number N of waves having the established duration, operation continues to step 128. If N is greater than or equal to two or less than or equal to sixteen, the crackle counter is incremented, step 130, counter N is reset, step 129, and operation continues, step 123, for identification of the remainder of the crackles in the sound sample. If N does not fall within this range, the group of waves is not identified as a crackle and the operation continues by resetting the counter, step 129, moving to the next wave, step 123, and looking for the next initial deflection wave, step 122.

FIG. 3B illustrates an additional two steps which may be added to the embodiment of FIG. 3A for identifying waves only if their durations progressively increase. Steps 125 and 127 may be added after step 122 for incrementing wave counter N after identification of the first or initial deflection wave only if the duration of the wave is greater than the previous wave duration. This provides the further limitation that the waves of the adventitious sound must progressively increase in duration.

FIG. 3C illustrates steps which may be added to the embodiment of FIG. 3A for identifying an adventitious sound (in this case a crackle) only if the artifact duration is within set duration parameters. After identification of N waves potentially comprising a crackle, step 128, operation would proceed to step 131, in which the duration parameters for the different types of adventitious sounds would be set by the operator or retrieved from a preestablished memory location. Duration ranges for some of the types of adventitious sounds have been detailed above.

In step 132, the artifact duration is determined, and compared to the established artifact duration parameters, step 134. In this example, only crackles are being monitored. However, typically the system and method of this invention contemplate monitoring for numerous types of advantitious sounds; in that case, steps similar to step 134 would be added for comparison of the established artifact duration to the duration parameters for the other types of adventitious sounds. Operation then proceeds to step 129 if the duration is not in the desired range, or step 130 if it is.

The dominant frequency may also be used as a means of identification, preferably together with the overall sound duration. The frequency is determined using the half-cycle duration criteria by, for example, setting a minimum and maximum individual wave duration window for sequential wave comparison. For example, to count waves having a frequency of less than 350 hertz, the duration parameters are set as greater than approximatly 1.4 milliseconds per half cycle. For 350-500 hertz, the duration must be between approximately 1.0 and 1.4 milliseconds. Using the frequency criterion, one may distinguish between squeaks and squawks as a first, high-pitched group, and wheeezes and rhonchi as a second, low-pitched group. Wheezes and rhonchi may be individually distinguished based on the existence of two dominant frequencies in a wheeze; while both have a dominant frequency between 0-350 hertz, the wheeze has a second sound or note between approximately 350-500 hertz. These measurements, together with the overall duration based on number of consecutive waves, provide a further means of identifying the several types of adventitious sounds.

Figure 4A:
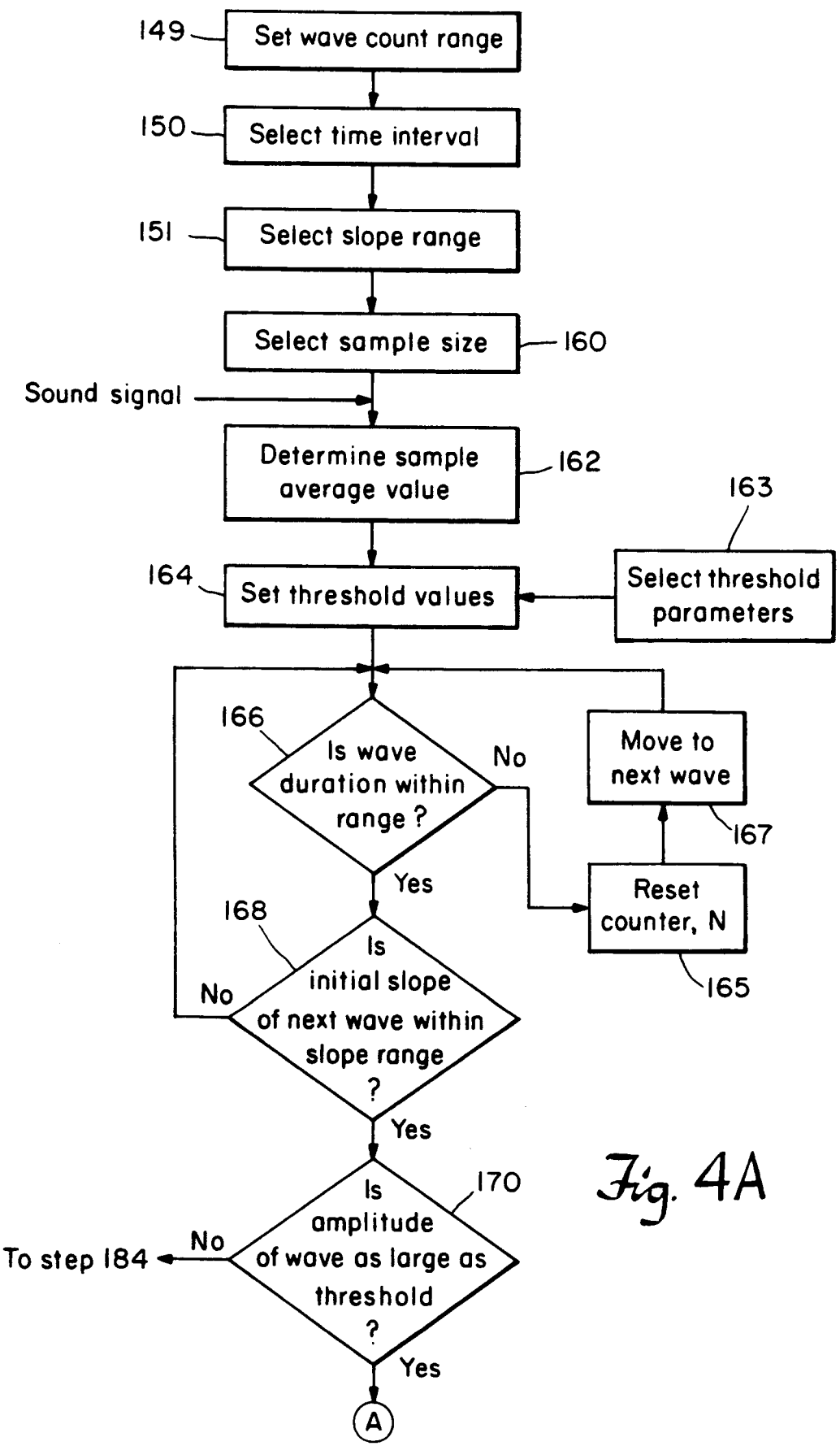
Figure 4B:
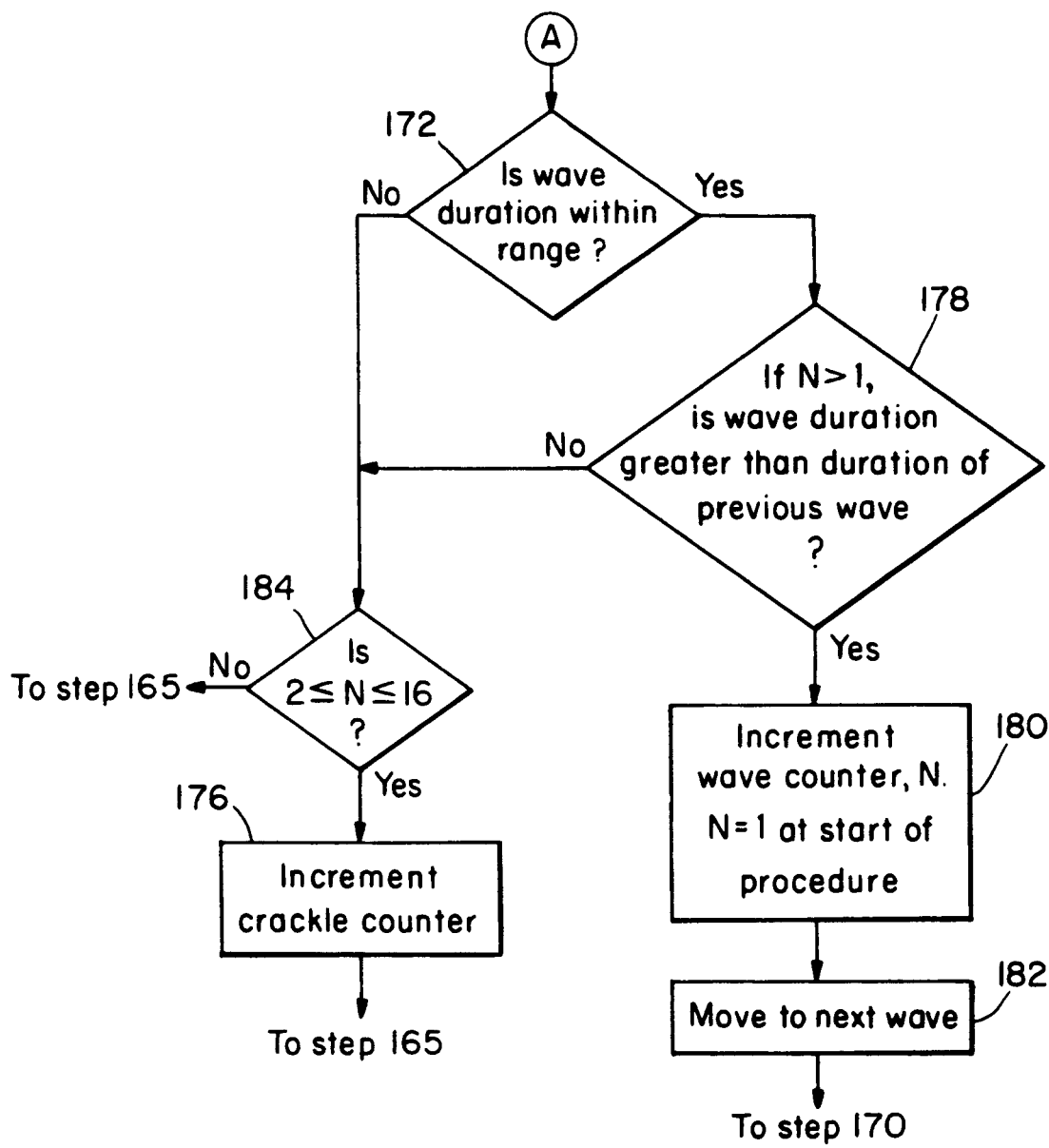

FIGS. 4A and 4B illustrate a flow chart of an embodiment of the present invention in which adventitious sounds are identified by comparison of the individual sound waves of the sound signal to several of the parameters which form a part of this invention. The operator selects a wave count range for identification of an adventitious sound, step 149, time interval for comparison to the wave duration, step 150, and a slope range for the initial slope of the wave following the initial deflection wave, step 151. The operator also selects the sample size, step 160. After a determination of an average value of the sample, step 162, the threshold values are set, step 164, in response to a selection of the threshold parameter, step 163. The individual waves of the sound signal are then sequentially examined starting with step 166.

Steps 166 and 167 together provide sequential comparison of the duration of the half cycle sound waves of the sound signal to the selected time interval. When a first wave having duration falling within the time interval is found, the system recognizes that an adventitious sound may be occurring. At step 168 the system compares the initial slope of the wave immediately following the initial deflection wave with the slope range. If the slope is within the range, operation proceeds to step 170. If the slope is not within the range, the duration of that wave is compared to the selected time interval, step 166, to determine if that next wave may also be an initial deflection wave.

If the slope is correct, the amplitude of that next wave is then compared to the threshold values, step 170. If the wave has an amplitude of less than the threshold values, operation proceeds to step 184. If the amplitude is at least as large as the threshold, operation proceeds to step 172 in which the wave duration is compared to the established time interval. If the wave duration falls within the established time interval, the duration of that wave is then compared to the duration of the previous wave; if the duration has increased, step 178, operation proceeds to step 180 where wave counter N is incremented. Step 178 is included only after identification of the initial deflection wave; the duration of that wave is not compared to the previous wave duration. Thus, to be identified as a half wave of a potential adventitious sound, each wave after the initial deflection wave must have an amplitude at least as large as the threshold value, a duration falling within the established time interval, and a duration greater than that of the previous wave.

If the wave duration is not within the established range, step 172, or if the wave duration is not greater than the previous wave duration, step 178, operation proceeds to step 184, in which the number of identified waves N following the initial deflection wave is compared to a predetermined wave count range. As an example, if N is greater than or equal to two or less than or equal to sixteen, operation proceeds to step 176 in which the crackle counter is incremented. The operation would then proceed to step 165 to resent counter N and begin looking for the next initial deflection wave. If the number of identified waves does not fall within the specified range, operation proceeds to steps 165 and 167 for counter reset and to start the search for the next initial deflection wave.

Figure 5:
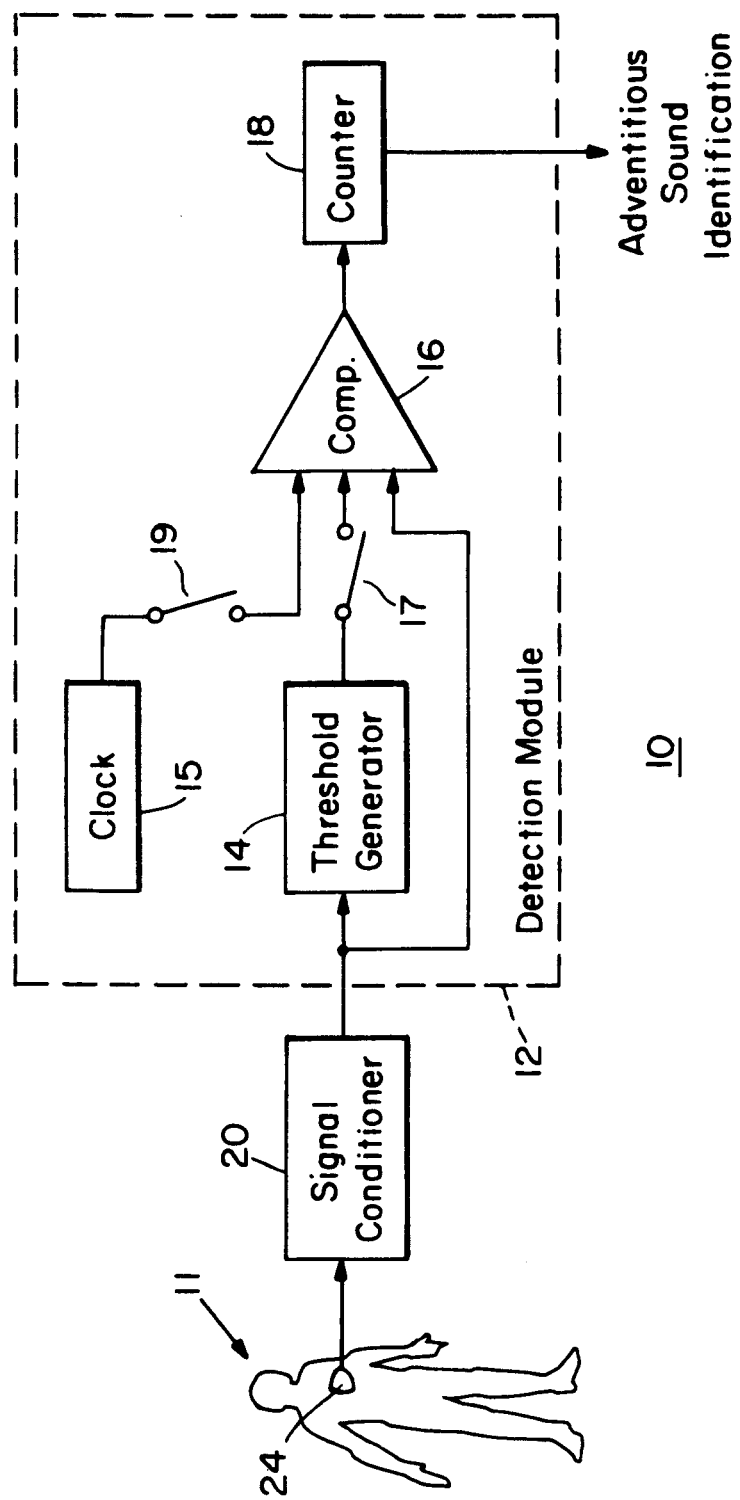
FIG. 5 is a simplified schematic diagram illustrating a system according to this invention for automatically identifying an adventitious lung sound in a patient.

Detection system 10 according to this invention is shown in FIG. 5. System 10 automatically identifies a selected type of adventitious sound occurring in a sound signal obtained from patient 11. Microphone device 24 which may be an electronic stethoscope is employed for detecting lung sounds. The lung sounds are fed to signal conditioner 20, which converts the sounds into corresponding electrical signals, for example signal 39, FIG. 1. Signal conditioner 20, FIG. 5, also amplifies the signal and attenuates normal sounds as is more fully described below. The output of signal conditioner 20 fed to detection module 12 consists of a plurality of half cycle sound waves.

Detection module 12 includes threshold generator 14, which determines an average signal value of at least a portion of the sound signal. Preferably, the average signal value is based on an entire respiratory cycle-inspiration and expiration. The average signal value may be based on the root mean square of the sample. Threshold generator 14 then generates positive and negative threshold values, having the same absolute value, based on that average signal value. As an example, the threshold values may be approximately three times the average signal value.

Comparator 16 is responsive to threshold generator 14, the signal from signal conditioner 20, and a signal from clock 15. Switches 19 and 17 are included for enabling or disabling clock 15 and generator 14, respectively. This provides the ability for comparator 16 to sequentially compare the sound waves of the sound signal to a predetermined time interval from clock 15 and/or the predetermined threshold values from threshold generator 14. Counter 18 then counts the number of waves satisfying the amplitude and/or duration criteria for identifying an adventitious sound when a preselected number of waves are counted.

Figure 6:
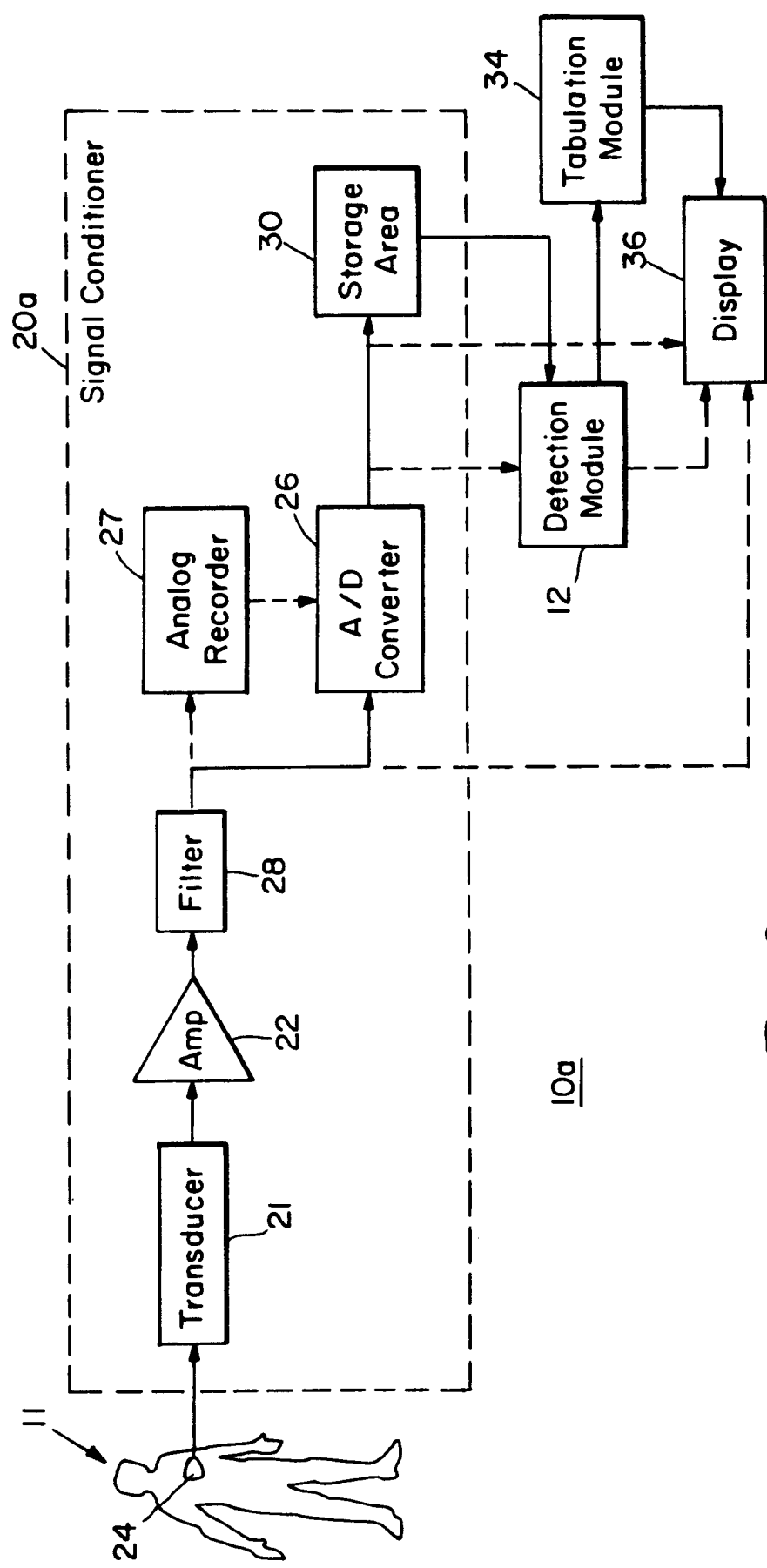
FIG. 6 is a more detailed schematic diagram of the system of FIG. 5 featuring the signal conditioner.

System 10a is shown in more detail in FIG. 6, in which signal conditioner 20a includes transducer 21 for converting detected sounds into corresponding electrical signals. Amplifier 22 amplifies those signals and the amplified signal is passed through filter 28 for attenuating "normal" sounds. Filter 28 may be chosen to filter out signals in a desired frequency range. As an example, filter 28 may filter signals below approximately 80 hertz and above approximately 2000 hertz; it has been found that adventitious sounds typically have frequencies between 80 and 2000 hertz. The filtered sound signal may then pass to analog recorder 27 to provide storage for later analysis, either by an experienced observer or automatically by detection module 12.

The filtered signal is digitized by A/D converter 26 and stored in storage area 30. Detection module 12 retrieves the stored sample from storage area 30 to identify the selected type of adventitious sound. Alternatively, detection module 12 may directly receive the sound signal from converter 26.

Adventitious sounds detected by module 12 are fed to tabulation module 34 for counting the number and/or determining the frequency of adventitious sounds occurring in the sound signal. A statistical summary of that information can be generated and displayed on display 36. That display may include, for example, the number of abnormal or adventitious lung sounds that had been detected at each of a number of locations on a patient's chest, as well as the frequency of detection of those sounds at each such location.

Alternatively, display 36 may be connected directly to detection module 12 for indicating when an adventitious sound has been detected. Display 36 may also receive and display digital or analog sound signals from converter 26 or filter 28, respectively.

Detection module 12a is shown in more detail in FIG. 7. The conditioned signal from signal conditioner 20, FIG. 5, passes to duration comparators 23 and 32 and threshold generator 14a. Comparator 23 compares the duration of each individual wave to a predetermined time interval and passes that information to initial deflection wave identifier 25. Identifier 25 identifies an initial deflection wave when its duration falls within the preselected time range. For detection of crackles, that time range may be chosen to be from approximately 0.125 to approximately 3.0 milliseconds; that number was determined from manual analysis of a large number of sound signals in which adventitious sounds had been identified by skilled technicians and doctors.

Slope analyzer 29 is enabled by identifier 25 and is responsive to the input signal for comparing the initial slope of the wave immediately following the initial deflection wave with a preselected range of wave slopes. That range of slopes may readily be determined by one skilled in the art from analysis of the output of filter 28, FIG. 6, which may be observed on display 36, for example as shown in FIG. 1. As a non-limiting example of a range of slopes which has been found to be indicative of the first wave of a crackle, if A/D converter 26, FIG. 6, is a twelve bit converter and a ten volt scale is used, each digital value represents ten over 4096 or approximately 0.0024 volts. If the digital signal is sampled every eight thousandths of a second (8K sample rate), the difference between the first value after the zero crossing and the next value, in other words, the change in one eight thousandth of a second, must be between 375 to 400 of those digital units.

Duration comparator 32 is enabled by slope analyzer 29 for comparing the duration of the wave whose slope was just checked to the predetermined time interval. Preferably, amplitude comparator 33 is enabled by duration comparator 32 for comparing the wave amplitude to the threshold values only when it has a duration falling within the desired range. Duration comparator 32 may also compare the wave duration to the duration of the previous wave to enable comparator 33 only when the wave duration is greater than that of the previous wave, but still falls within the predetermined time interval. Alternatively, amplitude comparator 33 may be responsive to initial deflection wave identifier 25 for analysis based on wave amplitude alone.

In another embodiment, duration comparator 32 may be responsive to amplitude comparator 33 for identifying waves of a potential adventitious sound by the established wave criteria only after a first wave having an amplitude at least as large as a threshold value is found. In any case, comparator 33 successively compares the waves to the threshold values and identifies a wave only when its amplitude is as large as a threshold value. Wave count comparator 35 is responsive to comparator 33 and/or comparator 32 for counting the number of waves satisfying the duration and/or amplitude criteria. Adventitious sound identifier 37 is responsive to comparator 35 for identifying an adventitious sound only when the number of waves falls within a predetermined range, which may be between two and sixteen waves for a crackle. Counter 39 then counts the number of adventitious sounds identified in the sound sample.

Figure 8A:
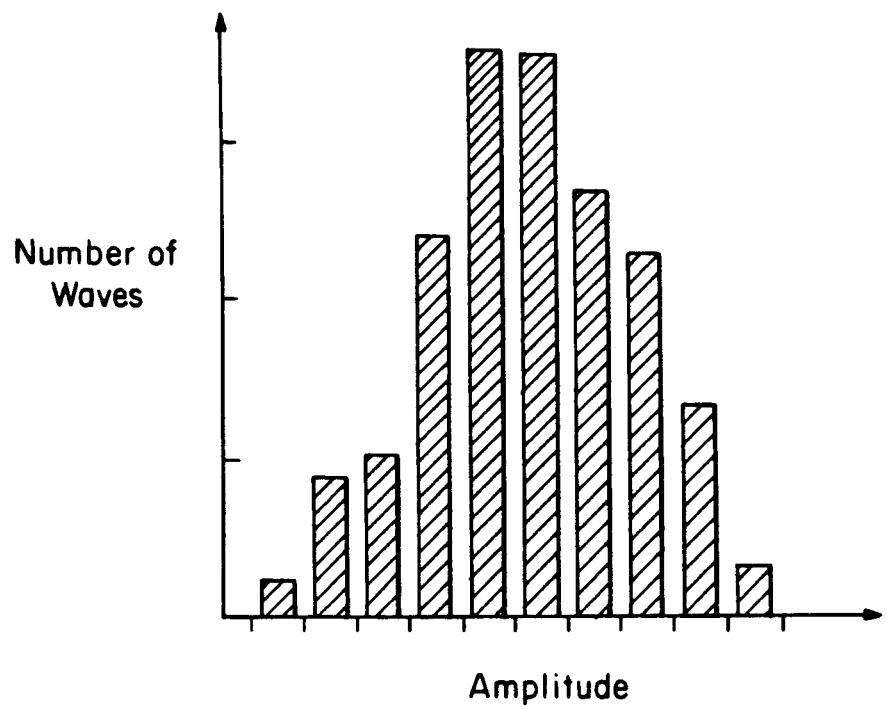
FIGS. 8A, B and C are plots of the relative wave amplitude distributions in a normal lung sound, crackle and rhonchus, respectively, illustrating the amplitude detection method of adventitious lung sound identification according to this invention.
Figure 8B:
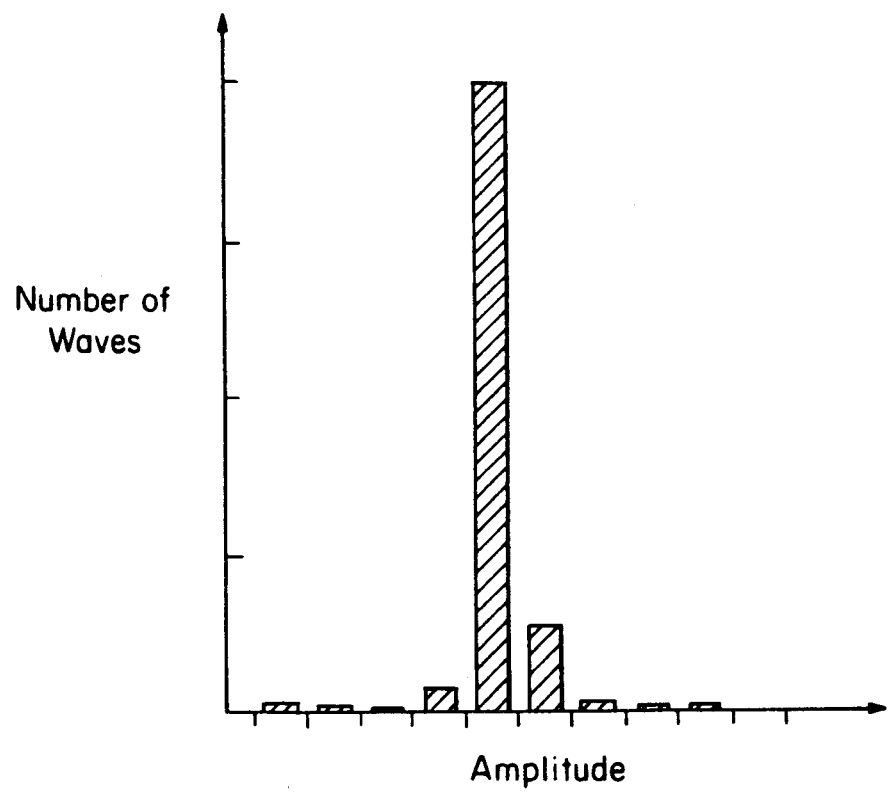
Figure 8C:
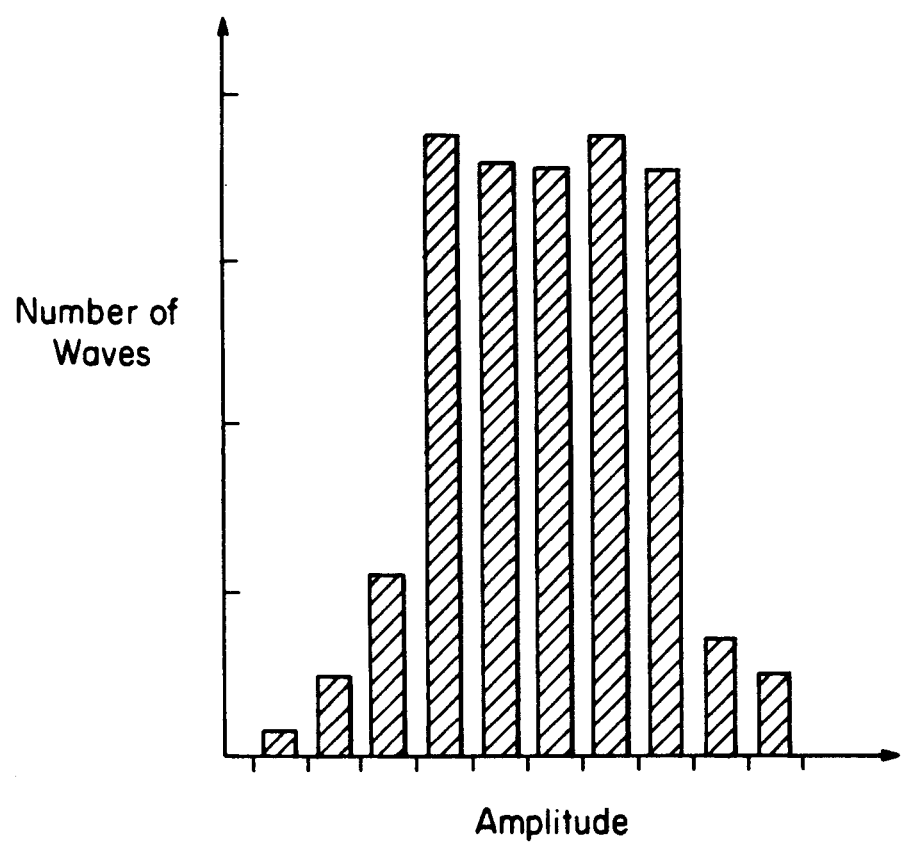

FIG. 8A is a plot of the half cycle sound wave amplitude distribution for a normal lung sound, in which the distribution is Gaussian in nature. In FIG. 8B is shown a similar plot for a crackle, showing that the vast majority of the waves have similar amplitudes. Finally, FIG. 8C illustrates a similar plot for a rhonchus, showing that a rhonchus has a wide and relatively even wave amplitude distribution. The system and method according to this invention thus may be used to identify adventitious sounds based on a sound wave amplitude distribution comparison as described above in connection with FIG. 2C.

Although several embodiments have been described, especially in relation to identification of a crackle, other adventitious sounds such as wheezes, rhonchi, squeaks, squawks, pleural friction rub, and bronchial breathing can similarly be identified by the system and method of the present invention. The adventitious sounds may be identified in a number of ways; in one embodiment, an adventitious sound is found by identifying a first wave having an amplitude at least as large as a threshold value and counting the number of sequential following waves having that amplitude. The amplitude distribution may also be employed in adventitious sound identification. Alternatively, the duration of the following waves may be compared to the predetermined time interval to identify waves only when their duration falls within that time interval.

In another embodiment, an initial deflection wave is first identified by sequentially comparing the durations of the waves to the predetermined time interval. After the first or initial deflection wave having a duration falling within the predetermined time interval is found, the number of sequential waves having either durations falling within that range or amplitudes at least as large as the threshold values is determined. Also, the duration of the event may be compared to typical durations for the different types of adventitious sounds.

It should be understood that either the amplitude or duration identification, or both, may be employed in identifying waves of a potential adventitious sound. Additional criteria which may be established for identification of waves of an adventitious sound are the initial slope of the first wave after the initial deflection wave, and the progressive duration criterion detailed above.

Also, the number N of sequential waves satisfying the chosen criteria may be chosen as desired to allow the system and method of this invention to identify groups of waves as adventitious sounds in accordance with the overall criteria established by one skilled in the art. By providing for a choice among these parameters, the system and method according to this invention may be tailored as necessary to identify different types of adventitious sounds based on previous expert identification and analysis of those types of sounds.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A system for automatically detecting an adventitious sound from a sound signal formed of a plurality of successive sound waves received from a patient, comprising:

means for sequentially comparing the individual sound waves of at least a portion of the sound signal with a first predetermined time interval to identify an initial deflection wave having a duration falling within said first predetermined time interval; and means, responsive to said means for comparing, for identifying an adventitious sound occurring within said sound signal when each of from 2-16 consecutive sound waves following said initial deflection wave has a duration falling within a second predetermined time interval.

2. A system for automatically detecting an adventitious sound in a sound signal formed of a plurality of successive sound waves received from a patient, comprising:

means for establishing at least one of a predetermined time interval and a threshold signal value based on an average signal value of at least a portion of said sound signal;

means, responsive to said means for establishing, for sequentially comparing said sound waves to at least one of said threshold signal value and said predetermined time interval to identify a first wave having at least one of an amplitude at least as large as said threshold signal value and a duration falling within said predetermined time interval;

means, responsive to said means for sequentially comparing, for identifying an adventitious sound when at least one consecutive wave following said first wave has at least one of an amplitude at least as large as said threshold signal value and a duration falling within said predetermined time interval; and means for conditioning said sound signal to attenuate normal sounds, including a filter for attenuating sound signals having frequency lower then approximately 80 hertz and greater than approximately 2000 hertz.

3. The system of claim 2 in which said means for conditioning includes means for digitizing said sound signal.

4. The system of claim 2 in which said means for conditioning includes means for amplifying said sound signal.

5. The system of claim 2 in which said means for conditioning includes means for storing a sample sound signal.

6. The system of claim 5 in which said sample sound signal includes an analog sound signal sample.

7. A system for automatically detecting an adventitious sound in a sound signal formed of a plurality of successive sound waves received from a patient. comprising:

means for establishing at least one of a predetermined time interval and a threshold signal value based on an average signal value of at least a portion of said sound signal;

means, responsive to said means for establishing, for sequentially comparing said sound waves to at least one of said threshold signal value and said predetermined time interval to identify a first wave having at least one of an amplitude at least as large as said threshold signal value and a duration falling within said predetermined time interval;

means, responsive to said means for sequentially comparing, for identifying an adventitious sound when at least one consecutive wave following said first wave has at least one of an amplitude at least as large as said threshold signal value and a duration falling within said predetermined time interval; and means, responsive to said means for identifying, for determining the type of adventitious sound occurring in said sound signal.

8. The system of claim 7 in which said means for determining includes means for establishing the duration of the adventitious sound.

9. The system of claim 8 in which said means for determining further includes means, responsive to said means for establishing, for identifying a squeak or squawk if said adventitious sound duration is between 25 and 250 milliseconds.

10. The system of claim 8 in which said means for determining further includes means, responsive to said means for establishing, for identifying a wheeze or rhonchus if said adventitious sound duration is greater than 250 milliseconds.

11. The system of claim 8 in which said means for determining further includes means, responsive to said means for establishing, for identifying a crackle if said adventitious sound duration is less than 25 milliseconds.

12. A system for automatically detecting an adventitious sound from a sound signal formed of a plurality of successive sound waves received from a patient, comprising:

means for determining an average signal value of at least a portion of said sound signal;

means for generating a threshold value based on said average signal value;

means for sequentially comparing the sound waves of at least a portion of the sound signal with a predetermined time interval to identify an initial deflection wave having a duration falling within said time interval;

means, responsive to said means for sequentially comparing, for sequentially comparing the amplitude of individual sound waves following said initial deflection wave to said threshold value;

means, responsive to said means for sequentially comparing sound waves amplitude for identifying an adventitious sound occurring within the sound signal when each of a plurality of consecutive sound waves following said initial deflection wave has an amplitude at least as large as said threshold value; and means for determining the initial slope of the wave following said initial deflection wave.

13. The system of claim 12 further including means, responsive to said means for determining the initial slope, for comparing the initial slope with a predetermined slope range to identify a wave following said initial deflection wave having an initial slope falling within the slope range.

14. The system of claim 13 in which said means for identifying is further responsive to said means for comparing the initial slope for identifying an adventitious sound only when the initial slope of the wave following said initial deflection wave is within said slope range.

15. A system for automatically detecting an adventitious sound signal formed of a plurality of successive sound waves required from a patient, comprising:
means for establishing and a threshold signal value based on an average signal value of at least a portion of said sound signal;
means, responsive to said means for establishing, for sequentially comparing said sound waves to at least one of said threshold signal value and said predetermined time interval to identify a first wave having at least one of an amplitude at least as large as said threshold signal value and a duration falling within said predetermined timer interval;
means, responsive to said means for sequentially comparing, for identifying an adventitious sound when at least one consecutive wave following said first wave has at least one of an amplitude at least as large as said threshold signal value and a duration falling within said predetermined timer interval; and
means, responsive to said means for identifying, for determining the number of lung sounds in said sound signal.

16. A system for automatically detecting an adventitious sound signal formed of a plurality of successive sound waves received from a patient, comprising:
means for establishing at least one of a time interval consisting of a series of predetermined time intervals which progressively increase in duration and a threshold signal value based on an average signal value of at least a portion of said sound signal;
means, responsive to said means for establishing, for sequentially comparing said sound waves to at least one of said threshold signal value and said predetermined time interval to identify a first wave having at least one of an amplitude at least as large as said threshold signal value and a duration falling within said predetermined time interval; and
means, responsive to said means for sequentially comparing, for identifying an adventitious sound when at least one consecutive wave following said first wave has at least one of an amplitude at least as large as said threshold signal value and a duration falling within said predetermined time interval.

17. A system for automatically detecting an adventitious sound from a sound signal formed of a plurality of successive sound waves received from a patient, comprising:
means for determining an average signal value of at least a portion of said sound signal;
means for generating a threshold value based on said average signal value;
means for sequentially comparing the sound waves of at least a portion of the sound signal with a predetermined time interval to identify an initial deflection wave having a duration falling within said time interval;
means, responsive to said means for sequentially comparing, for sequentially comparing the amplitude of individual sound waves following said initial deflection wave to said threshold value;
means for comparing the total sum of waves including the initial deflection wave and the number of consecutive sound waves after said initial deflection wave having an amplitude at least at large as said threshold value to a predetermined wave count range between three to sixteen waves; and
means, responsive to said means for sequentially comparing sound wave amplitudes and responsive to said means for comparing, for identifying an adventitious sound occurring within the sound signal when each of a plurality of consecutive sound waves following said initial deflection wave has an amplitude at least as large as said threshold value and for identifying an adventitious sound only when said sum total of waves is within said predetermined wave count range.

18. A system for automatically detecting an adventitious wound from a sound signal formed of a plurality of successive sound waves received from a patient, comprising:
means for determining an average signal value of at least a portion of said sound signal;
means for generating a threshold value based on said average signal value;
means for sequentially comparing the sound waves of at least a portion of the sound signal with a predetermined time interval to identify an initial deflection wave having a duration falling within said time interval;
means, responsive to said means for sequentially comparing, for sequentially comparing the amplitude of individual sound waves following said initial deflection wave to said threshold value;
comparator means for sequentially comparing at least a portion of the sound waves following said initial deflection wave with said predetermined time interval;
counter means, responsive to said comparator means, for resolving the number of consecutive sound waves following said initial deflection wave having a duration falling within said predetermining time interval;
means for comparing the duration of said consecutive sound waves having a duration falling within said predetermined time interval to the duration of the previously occurring sound wave; and
means, responsive to said means for sequentially comparing the sound waves, responsive to said means for sequentially comparing sound waves amplitudes and responsive to said means for comparing the duration of said consecutive sound waves, for identifying an adventitious sound occurring within the sound signal when each of a plurality of consecutive sound waves following said initial deflection wave has an amplitude at least as large as said threshold value and for identifying an adventitious sound only when a plurality of successive sound waves following said initial deflection wave have progressively increasing durations.

19. A system for automatically detecting an adventitious sound from a sound signal formed of a plurality of successive sound waves received from a patient, comprising:

means for determining an average signal value of at least a portion of said sound signal;

means for generating a threshold value based on said average signal value;

means for sequentially comparing the sound waves of at least a portion of the sound signal with a predetermined time interval from between approximately 0.125 to approximately 3.0 milliseconds to identify an initial deflection wave having a duration falling within said time interval;

means, responsive to said means for sequentially comparing, for sequentially comparing the amplitude of individual sound waves following said initial deflection wave to said threshold value; and means, responsive to said means for sequentially comparing the sound waves and sound wave amplitudes, for identifying an adventitious sound occurring within the sound signal when each of a plurality of consecutive sound waves following said initial deflection wave has an amplitude at least as large as said threshold value.

* * * * *